United States Patent [19]

Gruber et al.

[11] 4,055,590

[45] Oct. 25, 1977

[54] METHOD OF MAKING CARBOXYLIC ACID ESTERS

[75] Inventors: Wilhelm Gruber, Darmstadt; Guenter Schroeder, Ober-Ramstadt, both of Germany

[73] Assignee: Rohm GmbH, Darmstadt, Germany

[21] Appl. No.: 698,676

[22] Filed: June 22, 1976

[30] Foreign Application Priority Data

June 26, 1975 Germany ............................ 2528524

[51] Int. Cl.² ............................................. C07C 69/66
[52] U.S. Cl. .................................... 560/179; 560/212; 560/96; 560/265; 560/190; 560/187; 560/205
[58] Field of Search ............ 260/484 R, 475 R, 485 R

[56] References Cited

PUBLICATIONS

Szmant, H. H., Organic Chemistry, p. 425 1957.

*Primary Examiner*—Paul J. Killos
*Attorney, Agent, or Firm*—Curtis, Morris & Safford

[57] ABSTRACT

In a method for making a carboxylic acid ester by the reaction of the corresponding carboxylic acid amide with a primary alcohol in the presence of a catalyst at elevated temperature, the improvement wherein said catalyst is an at least partially dissolved metal carboxylate or a compound forming a metal carboxylate by reaction in situ with a carboxylic acid, the anion of which metal carboxylate is the anion of said carboxylic acid.

5 Claims, No Drawings

METHOD OF MAKING CARBOXYLIC ACID ESTERS

The present invention relates to a method for making carboxylic acid esters by the reaction of carboxylic acid amides with an alcohol in the presence of a catalyst.

The alcoholysis of acid amides has been known for a long time and was described as early as 1889 by Lothar Meyer in "Berichte der deutschen chemischen Gesellschaft" 22, 24 et seq. Meyer also noticed that the reaction could be accelerated by small amoumts of acid impurities in the amide, although conversions of only 42–44 percent were reached in 24 hours. Since even the ester formed by the reaction undergoes side-reactions with ammonia present in the system, forming a number of products including ammonium carboxylate, the acid must also be present as the ammonium salt. These salts are unstable at the temperatures of about 200° C. used in the present invention, decomposing to the free acid and ammonia.

Many carboxylic acid esters are known to be technically valuable products which, for example, are prepared on a technical scale as solvents or also as intermediate products. By way of example, it can be mentioned that methyl acetate, prepared by the reaction of acetamide with methanol, is a product prepared on an industrial scale and that α-hydroxy isobutyric acid methyl ester, obtained from α-hydroxyisobutyramide by reaction with methanol, can be converted by dehydration to methyl methacrylate, which also is used on a large scale.

For carrying out the last-mentioned process, many catalysts are known in the patent literature (mentioned by way of example are U.S. Pat. No. 2,184,934, Russian Pat. No. 143,389, and German patent publication Nos. DAS 1,191,367, DAS 1,211,153, and DAS 1,033,656), so that the conversion of the methyl ester of α-hydroxy isobutyric acid, obtained according to the present invention from α-hydroxy isobutyramide and methanol, to methyl methacrylate can be viewed as solved on a technical scale.

The first process step in the preparation of methyl methacrylate, namely the catalytically promoted hydration of acetone cyanohydrin to form α-hydroxy isobutyramide, is also known and is described, for example, in German Pat. No. 2,131,813. This latter process, characterized by the use of pyrolusite as a catalyst, belongs to a broader state of the art which generally pertains to the hydration of nitriles. An entire series of compounds active as catalysts for the preparation of amides from the corresponding nitriles is known. In U.S. Pat. No. 2,421,030, for example, a $SiO_2-Al_2O_3$ catalyst is described for the preparation of acetamide from acetonitrile. According to U.S. Pat. No. 3,062,883, nitriles having 2-6 carbon atoms can be hydrated to form the corresponding amides in the presence of a strongly basic anion exchange resin at temperatures from 50°–120° C. Catalysts which contain metals of Group IIB or Group VII of the Periodic System are described in U.S. Pat. No. 3,670,021 as catalysts for the process in question. Further catalysts for the conversion of nitriles to the corresponding amides are the subject of U.S. Pat. No. 3,673,250.

The process which is the subject of the present invention was first investigated because, in the preparation of methyl methacrylate from acetone, hydrocyanic acid, and methanol using the aforementioned intermediate steps, the step of alcoholysis of the α-hydroxy isobutyramide to the methyl ester of α-hydroxyisobutyric acid has not yet satisfactorily been solved on a technical scale. On further investigation of the process in question, it was discovered that the selection principle for the catalyst favoring the alcoholysis of α-hydroxyisobutyramide was valid for the alcoholysis of carboxylic acid amides generally.

It was found that the reaction of a carboxylic acid amide with an alcohol with formation of the corresponding ester is favored to a surprising degree by the presence of a metallic salt of the acid corresponding to the amide or the ester, dissolved in the reaction medium. It was also found that the carboxylate anion, as opposed to the salt-forming cation, had a greatly superior significance. In other words, to the extent there is at least partial solubility of the catalytically effective carboxylate, it is without significance — over wide limits — which metal cation is coordinated with the carboxylate anion primarily promoting the alcoholysis.

As is later shown in the Examples, it is not necessary to add to the reaction mixture a salt of whichever carboxylic acid is chosen. Rather, in most cases, the catalytically-active carboxylate is left to form in the reaction medium. The addition, later described in detail, of sodium methylate to an amide/alcohol mixture or to a solution of the amide in alcohol is typical, whereby sodium carboxylate forms quickly from the sodium alcoholate in an amount sufficient for catalysis of the reaction.

The requirement that the carboxylate must be at least in part soluble in the reaction medium excludes the use of such metal compounds, as starting materials for the formation of the catalytically active carboxylate, which are practically insoluble in the reaction medium. Examples of such compounds are the salts of strong acids in those cases where they are practically insoluble in the alcohol which is used, such as lead sulfate, but also sodium sulfate or sodium chloride. In other cases, salts of the aforementioned kind can be converted into soluble carboxylates by complex formation, as is true for example for lead chloride, which apparently is converted into a soluble catalytically-active compound by way of a lead chlorocarboxylate. It is also possible that a difficultly-soluble compound is reduced and then forms a suitable carboxylate. As examples, the nitrates of bismuth and chromium can be mentioned, which, apparently, form carboxylates suitable according to the invention by way of the formation of the corresponding nitrites as an intermediate stage.

It has already been mentioned that the metal cation has a much inferior significance to the anion from the point of view of catalytic activity. Extensive tests have shown that, according to expectation, there are gradual differences between carboxylates formed from the same acid but from different cations. The choice of the metal compounds to be used as starting materials is guided according to tests which determine the efficacy of the carboxylate which is formed from this starting compound and also by the price and the availability of the corresponding starting materials.

To the extent that a metal carboxylate of the carboxylic acid corresponding to the carboxylic acid amide is not added directly to the reaction mixture, other metal compounds are employed from which the corresponding carboxylates form under the reaction conditions. The formation of the carboxylate is made possible because of the small amounts of water always present in the reaction mixture and which, from the amide, forms the corresponding carboxylic acid. This is evident from the aforementioned work of Lothar Meyer. He observed an alkylation of the amide nitrogen atom with the liberation of water. He further determined the formation of ammonium carboxylates which, in any event, are unstable under the conditions of the aforementioned reaction and which decompose into ammonia and the free carboxylic acid.

If carboxylates of other carboxylic acids($R'—CO_2Me$) are added, the carboxylate of the free carboxylic acid ($R—CO_2H$) corresponding to the amide is formed, to an equilibrium point, according to the equation:

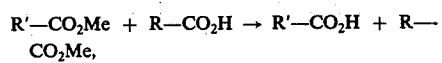

wherein Me can be a univalent metal cation or the charge-equivalent of a polyvalent metal cation.

If oxides, hydroxides, or carbonates of metals are added, the carboxylates are formed according to the equations

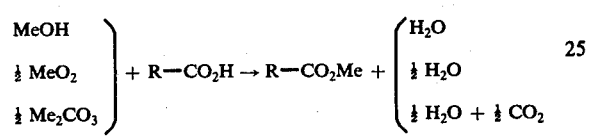

However, the catalytically-effective metal carboxylates can be formed from still other metal compounds if the metal compound is adaptable to hydrolytic cleavage, for example:

wherein X is the anion of an acid, for example a chloride or nitrate ion. The hydroxides react further in the aforementioned fashion. Compounds of polyvalent metals may, in some cases, not form the hydroxides, but basic salts:

$FeCl_3 + H_2O \rightarrow FeOHCl_2 + HCl$, which in a corresponding fashion react further to form mixed carboxylates:

$FeOHCl_2 + R—CO_2H \rightarrow FeCl_2(R—CO_2) + H_2O$.

In many cases, the metal carboxylates are formed directly from other salts according to the reaction:

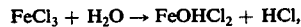

According to this reaction scheme, for example, the acetates of chromium, iron, zirconium, thorium, or uranium, are formed from acetic acid and chromium-II-chloride, iron-III-chloride, zirconium-IV-chloride, thorium chloride, or uranyl nitrate. This is evident from Beilstein, Handbuch der organischen Chemie, Vol. II, pages 110, 115, 117, 120, and 121.

In other cases, complex salts are formed according to the equation:

In the presence of acetic acid and ammonia, a copper-amine-acetate complex salt is formed from copper-II-chloride. It has not been explored which of the various possible reactions occur in individual cases. This depends naturally also on the solubility of the metal compound added and any intermediate stages which are possibly formed. The test results which are repeated below, which have been obtained for the reaction of oxyisobutyramide with methanol in the presence of different lead compounds, show yields which are in remarkable agreement and selectivity, which can be explained readily in all cases by the formation of lead oxyisobutyrate. Even metallic lead evidently is converted into this catalytically-effective compound in a sufficient amount.

In Table I reported below, all of the reactions were run at a temperature of 200° C. In each case, the lead compound contained 1 percent of Pb, by weight of the oxyisobutyric acid amide employed. The Table reports the yield of oxyisobutyric acid methyl ester formed. The selectivity is the yield of desired product calculated on the reacted oxyisobutyramide.

TABLE I

| Lead Compound | Reaction Time | Yield | Selectivity |
|---|---|---|---|
| Pb-II-oxyisobutyrate | 3 | 33.3 | 82 |
| PbO | 3 | 39.2 | 99.7 |
| $Pb_2(OH)(OCOCH_3)_3$ | 2 | 33.6 | 80.8 |
| $PbCl_2$ | 6 | 27.8 | 100 |
| $Pb(NO_3)_2$ | 6 | 33.5 | 71 |
| $PbO . PbCl_2$ | 6 | 32.9 | 87 |
| $Pb(OH)_2 . Pb(CO_3)_2$ | 6 | 29.6 | 68 |
| Pb-metal | 6 | 36.3 | 100 |

All of the tests were carried out in closed small autoclaves from which neither ammonia nor other reaction products could escape during the reaction. The tests were not carried out under the conditions most advantageous for the reaction, but were carried out under comparable conditions.

The process of the invention is advantageously carried out at temperatures which are above the boiling point of the alcohol which is used, i.e., the preparation of the carboxylic acid ester in most cases takes place, either discontinuously or continuously, in a pressure reactor, preferably at temperatures from about 150° C. to about 250° C. However, to the extent the alcoholysis of the invention is carried out with an alcohol whose boiling point is above the reaction temperature to be maintained, which, for example, is true for octyl alcohol and in a more notable degree for alcohols having more than 10 carbon atoms, proceeding in a pressure vessel can be avoided. This offers an advantage not only from the point of view of outlay for apparatus, but a greater advantage in that the ammonia formed by the alcoholysis can simultaneously continuously be removed from the reaction mixture. This condition favoring ester formation can be achieved in the preparation of esters of lower alcohols, which must be prepared in a pressure vessel, by an intermittent blowing off of the ammonia or by a partial depressurization of the reactor. In the case of a discontinuous process, it may become necessary to replace the alcohol escaping with the ammonia. When working in a continuous fashion, the amounts of alcohol escaping on partial depressurization can be taken into consideration in feeding the reaction mixture comprising amide and alcohol.

Since the preparation of carboxylic acids in by far the most cases takes place by a direct esterification of the free acid or by a trans-esterification of, for example, the methyl ester with a longer-chained alcohol, the process of the present invention is of significance only in those cases in which the acid amide is more easily obtainable than the acid. One of these technically interesting possibilities, namely the alcoholysis of α-hydroxy-isobutyric acid amide as an intermediate step in the preparation of methyl methacrylate from acetone, hydrocyanic acid, and methanol, has already been mentioned. Although at this time, several hundred thousand tons of this unsaturated acid are produced yearly practically exclusively by the reaction of acetone cyanohydrin with concentrated sulfuric acid and methanol, whereby the sulfate of methacrylamide — which is not isolated — is formed in an intermediate stage, the commercial exploitation of this process will more and more meet increasing difficulties because of the necessity of eliminating the "waste sulfuric acid", which forms as a by-product, in an environmentally-unobjectionable way. At an annual production of 100,000 tons of methyl methacrylate, about 160,000 tons of a "waste sulfuric acid" comprising ammonium bisulfate and free acid, contaminated with organic substances, are formed, the working up of which — with the loss of ammoniacal nitrogen — is extremely expensive because of the required observation of pertinent regulations. The process outlined above, in which the subject of the present invention represents a partial step, has a chance for future use since the aforementioned problem of avoiding waste acid does not occur.

Further technically interesting processes are the reaction of acetamide and methanol to form methyl acetate, the preparation of adipic acid esters from adipic acid diamide, the alcoholysis of acrylamide or methacrylamide with methanol or ethanol, and the preparation of terephthalic acid esters from terephthalic acid diamide.

The present application is directed to the use solely of monovalent and polyvalent primary alcohols, even though the reaction of a carboxylic acid amide with secondary and tertiary alcohols is also promoted by the catalysts according to the invention with respectively decreasing yields.

Following Examples 1–50, which relate to the methanolysis of α-hydroxy-butyramide, show the manifold possibilities, proceeding from very different compounds of numerous metals, for forming catalytically active metal carboxylates in a reaction medium. Further Examples 51–56 show the alcoholysis of other amides.

A better understanding of the present invention and of its many advantages will be had by referring to the following specific Examples, given by way of illustration.

A. Methanolysis of α-Hydroxy-isobutyramide General Experimental Procedure

A mixture of α-hydroxy-isobutyramide and methanol in a mol ratio of 1:10 was heated in an autoclave to 200° C. in the presence of catalytic amounts of metal compounds (mol percent calculated on the amide), and cooled for 6 hours. The reaction mixture was analyzed gas chromatographically. The results obtained with different metal compounds are evident from following Table II.

TABLE II

| Ex. | Compound | Mol Percent | Amide Conversion (%) | Yield of Ester (% of Theory) | Selectivity (%) |
|---|---|---|---|---|---|
| 1 | LiOH | 1 | 11.2 | 11 | 98 |
| 2 | LiOH | 3 | 21.8 | 15.4 | 70.6 |
| 3 | Na-methylate | 1 | 15.1 | 15 | 99 |
| 4 | Na-methylate | 5 | 45 | 39 | 86.7 |
| 5 | Na-tungstate | 1 | 20 | 18 | 90 |
| 6 | K-tert . butylate | 1 | 16.1 | 14.3 | 89 |
| 7 | KOH | 3 | 23.4 | 19.0 | 81.2 |
| 8 | Be(NO$_3$)$_2$ | 1 | 25.4 | 11.2 | 44.1 |
| 9 | CaCl$_2$ | 1 | 11.8 | 11.5 | 97.5 |
| 10 | Al-ethylate | 1 | 25 | 17 | 70 |
| 11 | Ga(NO$_3$)$_3$ . 8 H$_2$O | 0.7 | 34 | 32.4 | 95.3 |
| 12 | " | 1 | 58.4 | 53.8 | 92.1 |
| 13 | InCl$_3$ | 1 | 41.4 | 40.4 | 97 |
| 14 | TlOH | 1 | 23.4 | 21.2 | 90.6 |
| 15 | GeCl$_4$ | 1 | 18.5 | 13.9 | 75.1 |
| 16 | Sn(phenyl)$_4$ | 1 | 44.8 | 35 | 78 |
| 17 | SbCl$_3$ | 1 | 46.8 | 42.0 | 89.6 |
| 18 | Bi(NO$_3$)$_3$ | 1 | 52.6 | 51.6 | 98 |
| 19 | TeO$_2$ | 1 | 60.9 | 60.4 | 99.2 |
| 20 | H$_2$TeO$_4$ | 1 | 59.4 | 54.7 | 92.1 |
| 21 | CuCl | 1 | 19.2 | 19 | 99 |
| 22 | Zn(OH)$_2$ | 1.5 | 53.5 | 48.0 | 89.7 |
| 23 | Zn(OH)$_2$ | 1 | 36 | 31 | 86 |
| 24 | ZnCl$_2$ | 1 | 30.8 | 26.6 | 86.4 |
| 25 | Cd-oxyisobutyrate | 2 | 33 | 31 | 94 |
| 26 | LaCl$_3$ | 1 | 58.2 | 57.3 | 98.3 |
| 27 | Ti(i-OC$_3$H$_7$)$_4$ | 1 | 42.4 | 40 | 94.4 |
| 28 | ZrOCl$_2$ . 8 H$_2$O | 1 | 38 | 36 | 94.7 |
| 29 | HfCl$_4$ | 3 | 52.2 | 36.8 | 70.5 |
| 30 | V$_2$O$_5$ | 1 | 42 | 49 | 85.7 |
| 31 | Ammonium vanadate | 1 | 29.2 | 28.9 | 98.3 |
| 32 | VCl$_2$ | 1 | 24.8 | 21 | 85 |
| 33 | NbCl$_5$ | 1 | 47.5 | 45.0 | 95.0 |
| 34 | TaCl$_5$ | 1 | 12.9 | 12.6 | 97.7 |
| 35 | Cr(NO$_3$)$_3$ | 1 | 23.1 | 16.9 | 73.3 |
| 36 | MoO$_3$ | 1 | 35.8 | 34.3 | 95.8 |
| 37 | WO$_3$ . H$_2$O | 1 | 51 | 47 | 92 |
| 38 | Mn(OAc)$_2$ . 4 H$_2$O | 1 | 32.9 | 26 | 79 |
| 39 | Mn-oxyisobutyrate | 1 | 32.5 | 30 | 92.2 |
| 40 | (NH$_4$)$_2$Ce(NO$_3$)$_6$ | 1 | 32.1 | 31.4 | 97.8 |
| 41 | Sm(NO$_3$)$_3$ . 5 H$_2$O | 1 | 49.5 | 47.0 | 95.0 |
| 42 | Th(NO$_3$)$_4$ | 1 | 10.6 | 10.5 | 99.5 |
| 43 | UO$_2$(OAc)$_2$ . 2 H$_2$O | 1 | 38.1 | 34.2 | 89.8 |
| 44 | UO(NO$_3$)$_2$ | 1 | 41.4 | 35.3 | 84.5 |
| 45 | FeCl$_3$ . 6 H$_2$O | 1 | 35 | 30 | 85.6 |
| 46 | Co(OAc)$_2$ . 4 H$_2$O | 1 | 30 | 20 | 66.7 |
| 47 | Co-oxyisobutyrate | 1 | 38.4 | 37.4 | 97.4 |

TABLE II-continued

| Ex. | Compound | Mol Percent | Amide Conversion (%) | Yield of Ester (% of Theory) | Selectivity (%) |
|-----|----------|-------------|----------------------|------------------------------|-----------------|
| 48  | $NiCl_2 \cdot 6 H_2O$ | 1 | 25.2 | 22.5 | 89.3 |

B. Reaction with Other Alcohols

EXAMPLE 49

20.6 g of α-hydroxy-isobutyramide and 92 g of ethyl alcohol were heated at 200° C. in an autoclave in the presence of 0.45 g of PbO for six hours. Gas chromatographic analysis showed that the α-hydroxy-isobutyric acid ethyl ester was formed in a yield of 62.7 percent of theory and with a selectivity of 95 percent.

EXAMPLE 50

A mixture of 20.6 g of α-hydroxy-isobutyramide and 204 g of n-hexyl alcohol was heated in the presence of 0.45 g of PbO for 6 hours at 200° C. in an autoclave. On working up by distillation, 19.5 g (= 51.8 percent of theory) of α-hydroxy-isobutyric acid-n-hexyl-ester were obtained. The amide conversion is 75 percent.

C. Alcoholysis of Other Amides

EXAMPLE 51

11.8 g of acetamide and 64 g of methanol were heated for 6 hours at 200° C. in an autoclave together with 0.45 g of PbO. Methyl acetate was obtained in a yield of 60.4 percent of theory with a selectivity of > 90 percent.

EXAMPLE 52

Analogously with the preceding Examples, 11.8 g of acetamide were reacted with 204 g of n-hexyl alcohol and worked up. The yield of n-hexyl acetate was 20.4 g (70.7 percent of theory).

EXAMPLE 53

28.8 g of adipic acid diamide and 64 g of methanol were reacted in the presence of 0.45 g of PbO according to Example 51. Adipic acid dimethyl ester was obtained in a yield of 57.6 percent of theory with a selectivity of 98 percent.

EXAMPLE 54

14.2 g of acrylamide and 64 g of methanol were reacted in the presence of $PbO_2$ as a catalyst in the same fashion as the preceding Examples. 53 percent of β-methoxypropionic acid methyl ester and 38 percent of β-methoxy propionic acid amide were obtained as the reaction products at a 99.2 percent acrylamide conversion.

EXAMPLE 55

Upon analogous reaction of 17 g of methacrylamide with 64 g of methanol, 12.3 percent of theory of methyl methacrylate was obtained at a selectivity of 99 percent.

EXAMPLE 56

32.8 g of terephthalic acid diamide and 64 g of methanol were heated together with 0.45 g of PbO for 5 hours at 250° C. Gas chromatographic examination of the reaction mixture showed that terephthalic acid dimethyl ester was formed in a yield of 36.7 percent of theory.

What is claimed is:

1. In a method for making a carboxylic acid ester by the reaction of the corresponding carboxylic acid amide with a primary alcohol in the presence of a catalyst at elevated temperature, the improvement wherein said catalyst is an at least partially dissolved metal carboxylate or a compound forming a metal carboxylate by reaction in situ with a carboxylic acid, the anion of which metal carboxylate is the anion of said carboxylic acid.

2. A method as in claim 1 wherein said carboxylate is formed in situ in the reaction medium.

3. A method as in claim 1 wherein a metal alcoholate or metal hydroxide is added to the reaction mixture.

4. A process as in claim 1 wherein α-hydroxy-butyramide is reacted with methanol.

5. A method as in claim 1 wherein the reaction is carried out in a pressure reactor at a temperature above the boiling point of the alcohol, and ammonia, formed during the reaction, is removed by intermittent or partial depressurization of the reaction vessel.

* * * * *